(12) United States Patent
Knapp

(10) Patent No.: US 6,672,870 B2
(45) Date of Patent: Jan. 6, 2004

(54) METHOD AND INSTRUMENTATION FOR ATTACHING DENTURES

(76) Inventor: John G. Knapp, 19928 Farmington Rd., Suite B-4, Professional Plaza, Livonia, MI (US) 48152

( * ) Notice: Subject to any disclaimer, the term of this patent is extended or adjusted under 35 U.S.C. 154(b) by 0 days.

(21) Appl. No.: 09/812,734

(22) Filed: Mar. 20, 2001

(65) Prior Publication Data

US 2002/0137003 A1 Sep. 26, 2002

(51) Int. Cl.[7] ............................... A61C 3/02
(52) U.S. Cl. ........................ 433/76; 433/75; 606/96
(58) Field of Search ..................... 433/76, 75; 606/96

(56) References Cited

U.S. PATENT DOCUMENTS

| | | | | |
|---|---|---|---|---|
| 2,181,746 A | | 11/1939 | Siebrandt ..................... 128/83 |
| 2,644,231 A | | 7/1953 | Brennan ......................... 32/2 |
| 3,407,503 A | * | 10/1968 | Nealon ......................... 433/76 |
| 3,414,975 A | | 12/1968 | Small ............................. 32/2 |
| 3,514,858 A | | 6/1970 | Silverman ....................... 32/2 |
| 3,562,913 A | * | 2/1971 | Saffro ......................... 433/75 |
| 3,664,022 A | | 5/1972 | Small ............................. 32/2 |
| 3,748,739 A | | 7/1973 | Thibert ...................... 32/10 A |
| 3,835,849 A | | 9/1974 | McGuire ................ 128/92 EB |
| 3,895,444 A | | 7/1975 | Small ......................... 32/10 A |
| 4,085,506 A | | 4/1978 | Lew .............................. 32/2 |
| 4,214,366 A | | 7/1980 | Laban ......................... 433/189 |
| 4,260,383 A | * | 4/1981 | Weissman ................... 433/225 |
| 4,325,373 A | | 4/1982 | Slivenko et al. ............. 128/303 |
| 4,360,012 A | | 11/1982 | McHarrie et al. ....... 128/92 EB |
| 4,364,381 A | | 12/1982 | Sher et al. ................ 128/92 E |
| 4,373,518 A | | 2/1983 | Kaiser et al. ........... 128/92 EB |
| 4,439,152 A | | 3/1984 | Small ......................... 433/173 |
| 4,475,890 A | | 10/1984 | Heidelbach ................. 433/173 |
| 4,479,271 A | | 10/1984 | Bolesky et al. .............. 3/1.911 |
| 4,516,937 A | | 5/1985 | Bosker ....................... 433/173 |
| 4,568,285 A | * | 2/1986 | Chiaramonte et al. ...... 433/173 |
| 4,608,972 A | | 9/1986 | Small ........................... 128/92 |

(List continued on next page.)

FOREIGN PATENT DOCUMENTS

| | | |
|---|---|---|
| CA | 848162 | 8/1970 |
| FR | 2 302 715 | 10/1976 |
| GB | 770696 | 11/1954 |
| GB | 37 369977 A1 | 7/1988 |
| GB | 2217 994 A | 11/1989 |
| GB | 2 252 911 A | 8/1992 |

OTHER PUBLICATIONS

Fixed mandibular complete denture prostheses supported by mandibular staple bone plate implant; John G. Knapp, D.D.S., M.S. and Irwin A. Small, D.D.S., Livonia, Michigan and Birmingham, Michigan, Jan. 1990.

Mandibular Staple Bone Plate/A Reconstructive Operation for the Endentulous Mandible; Surgical & Prosthetic Technique; Irwin A. Small, D.D.S. of Birmingham, Michigan and Alfred V. Stines, D.D.S. of Detroit, MI.

*Primary Examiner*—John J. Wilson
(74) *Attorney, Agent, or Firm*—Young & Basile, P.C.

(57) ABSTRACT

A method and apparatus for mounting a dental prosthesis to an upper or lower jaw of a patient. The apparatus includes a jig bushing and a base plate. The jig bushing has a plurality of apertures therethrough for guiding the travel of a drill bit for forming bores in the jaw of the patient. The base plate is immovably associated with the jig bushing and is formed to correspond to the shape of the jaw. A drill bit adaptor is provided for drilling bores in the ridge of the patient to an adjustable predetermined depth. The drill bit adaptor includes a plurality of annular recesses along a longitudinal length of the elongate body for receiving an E-ring. The body of the drill bit adaptor can be inserted into an aperture of the jig bushing until the E-ring presses against the jig bushing. Implants can be screwed into bores. Transmucosal adaptors having sloped ends can be added to each implant. Retaining screws can connect the implants with the transmucosal adaptors. The top plate can be seated on the sloped ends of the transmucosal adaptors.

14 Claims, 4 Drawing Sheets

U.S. PATENT DOCUMENTS

| | | | |
|---|---|---|---|
| 4,640,271 A | | 2/1987 | Lower .................... 128/92 |
| 4,648,841 A | | 3/1987 | Smith ..................... 433/173 |
| 4,710,075 A | * | 12/1987 | Davison .................. 408/202 |
| 4,713,077 A | | 12/1987 | Small ....................... 623/16 |
| 4,722,687 A | | 2/1988 | Scortecci ................. 433/165 |
| 4,784,608 A | | 11/1988 | Mays ........................ 43/172 |
| 4,906,189 A | | 3/1990 | Knapp ...................... 433/173 |
| 4,907,577 A | | 3/1990 | Wu ............................ 606/87 |
| 4,917,604 A | | 4/1990 | Small ....................... 433/174 |
| 4,931,016 A | | 6/1990 | Sillard ...................... 433/172 |
| 4,968,250 A | | 11/1990 | Small ....................... 433/173 |
| 4,988,297 A | | 1/1991 | Lazzara et al. ........... 433/173 |
| 4,998,881 A | * | 3/1991 | Lauks ........................ 433/76 |
| 5,221,204 A | | 6/1993 | Kruger et al. ............. 433/173 |
| 5,246,444 A | | 9/1993 | Schreiber .................. 606/87 |
| 5,306,278 A | | 4/1994 | Dahl et al. ................. 606/96 |
| 5,320,529 A | * | 6/1994 | Pompa ....................... 433/76 |
| 5,362,235 A | | 11/1994 | Daftary ..................... 433/172 |
| 5,376,004 A | * | 12/1994 | Mena ....................... 433/173 |
| 5,419,700 A | | 5/1995 | Sillard ..................... 433/172 |
| 5,503,557 A | | 4/1996 | Sillard ..................... 433/172 |
| 5,540,686 A | | 7/1996 | Zippel et al. ............... 606/57 |
| 5,554,027 A | | 9/1996 | Branemark ............... 433/172 |
| 5,556,278 A | * | 9/1996 | Meitner ..................... 433/75 |
| 5,688,283 A | | 11/1997 | Knapp ....................... 606/96 |
| 5,725,376 A | * | 3/1998 | Poirier ....................... 433/75 |
| RE35,784 E | | 5/1998 | Linkow et al. ........... 433/174 |
| 5,769,636 A | * | 6/1998 | Di Sario ..................... 433/75 |
| 5,785,525 A | | 7/1998 | Weissman ................. 433/174 |
| 5,890,897 A | * | 4/1999 | Kruger et al. ............... 433/75 |
| 5,915,962 A | * | 6/1999 | Rosenlicht ................. 433/76 |
| 5,967,783 A | | 10/1999 | Ura ........................... 433/174 |
| 5,984,681 A | | 11/1999 | Huang ...................... 433/174 |
| 5,989,025 A | * | 11/1999 | Conley ....................... 433/76 |
| 5,989,028 A | | 11/1999 | Niznick .................... 433/173 |

* cited by examiner

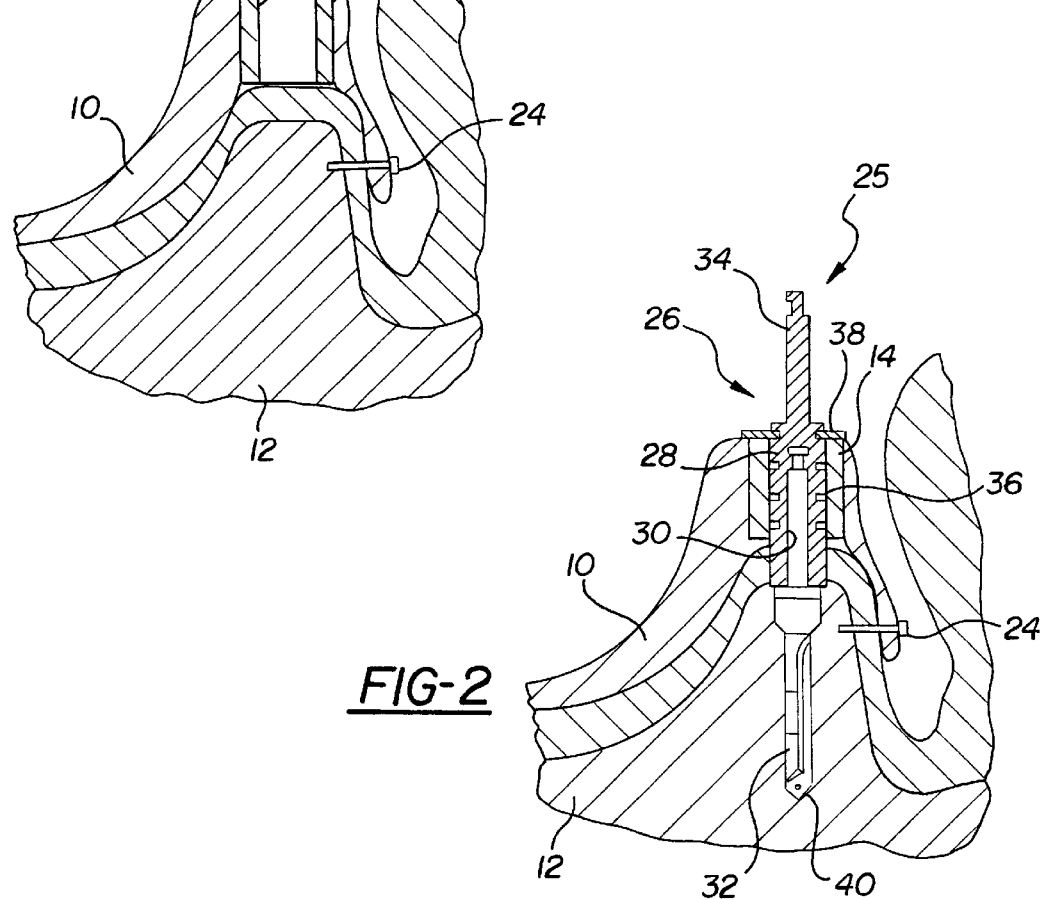

METHOD AND INSTRUMENTATION FOR ATTACHING DENTURES

FIELD OF THE INVENTION

The invention relates to a method and apparatus for attaching dentures.

BACKGROUND OF THE INVENTION

It is known to replace missing teeth in patients by implanting fixtures in the jawbone. In order to make the anchoring of the fixtures permanent, a number of requirements have to be met, including factors connected with the selection of materials and surgical technique. Fixtures in the form of screws are anchored in the jawbone by surgery and permitted to become integrated with bone tissue, a process known as osseointegration. The process of osseointegration is a healing process extending over a certain period of time.

The mounting of dental fixtures requires a tremendous amount of effort, resulting in relatively high costs for reconstruction of entire jaws. In addition, for each patient, the total time needed for reconstruction is prolonged. Therefore, it is desirable to reduce costs for reconstruction of entire jaws or for prosthetically reconstructing a continuous part of a row of teeth by application of user-friendly solutions aimed at reducing the time and work for implanting and mounting dental fixtures.

SUMMARY OF THE INVENTION

The present invention provides a simplified method for the fabrication of an implant supported fixed or removable dental prosthesis. It can be used to assist in the treatment of a totally or a partially edentulous patient. It can also be used with a prefabricated bar and clip apparatus for retaining an over-denture. The invention can be used in coordination with all root form implant designs and common or custom-made rotary instruments. The invention includes a base plate formed to correspond with the shape of the edentulous residual ridge of a specific patient. The base plate includes a large aperture. When the base plate is positioned on the ridge of the patient the aperture receives a jig bushing for guiding a rotary tool such as a drill bit or tapping device. The jig bushing can include multiple apertures.

The invention also provides a method for making the base plate. A casting of the patient's residual ridge can be created. A jig bushing can be positioned on the casting at a desired position. A supportive material can be used around the jig bushing on the casting and a formable material can be dispensed in the space formed between the jig bushing and the outline of the adjoining edentulous residual ridge or teeth. The dispensed material can harden to form the base plate. In order to maintain the position of the jig bushing relative to the casting as the formable material is dispensed, a bore can be drilled through one or more of the apertures in the jig bushing, into the casting, and a stabilizing pin can be inserted in the bore.

The invention also provides a method of using the base plate to perform an operation with respect to the patient's residual ridge. The base plate is formed to the shape corresponding to the ridge and any other surrounding structures as deemed necessary for stability and is engaged on the ridge. The engagement of the base plate with the ridge can be enhanced by positioning a rubber block between the base plate and the patient's opposing jaw, by action of a technical surgical assistant to hold the base plate in place or by drilling a bore through the base plate and into the patient's residual ridge and inserting a bone screw or nail. When the base plate is appropriately engaged with the patient's residual ridge, an operation can be performed. The operation can be a drilling or tapping or wedging operation.

The invention also includes a method and apparatus for drilling a bore of predetermined depth and direction into the patient's residual ridge at any position corresponding to an aperture in the jig bushing held by the base plate. The drilling apparatus can receive a plurality of different rotary tools for performing various operations with respect to the ridge. The depth that the drill travels into the patient's ridge can be controlled by a stopping means. The stopping means can include an annular recess formed along the length of a drill bit adaptor of the drilling means and an E-ring element receivable into the recess. When the plurality of bores are to be drilled into the patient's ridge, a stabilizing pin can be inserted into the bore created by the first drilling operation to enhance the engagement of the base plate with the ridge.

The invention also provides a method for mounting a dental prosthesis to the patient's residual ridge. After the bores have been drilled and taped into the patient's ridge an implant can be inserted into the bore. An extension adaptor can be mounted on the end of the implant. This extension fits to the end of the implant and penetrates through the depth of the adjacent mucosa extending into the mouth. The length of the extension corresponds to the depth of the placement of the implant and the desired height in the mouth. When a plurality of implants are so placed and connected with related extensions the implants will form an array of receiving terminal ends in the mouth. To these terminal ends, a top plate can be connected for use as a framework for a dental prosthesis.

The invention also includes a method for customizing a pre-machined top plate prosthodontic connector to be fastened to the receiving ends of the implants. A casting of the edentulous residual ridge with the plurality of implants and associated terminal ends for receiving the top plate can be created. A top plate can be positioned on the represented terminal ends and the plate can be custom modified with the attachment of appropriate dental materials to form a custom prosthesis.

Other applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein:

FIG. 1 is a cross-sectional view of a jig bushing mounted relative to the ridge of the patient;

FIG. 2 is a cross-sectional view of a bore being drilled into the patient's ridge;

FIG. 3 is a cross-sectional view of the bore drilled into the ridge of the patient;

DESCRIPTION OF THE PREFERRED EMBODIMENT

As shown in FIGS. 1-6, the present invention provides a base plate 10 formed to correspond approximately to the shape of a patient's maxilla (not shown) or mandibular ridge 12. The base plate 10 can engage jig bushing 14 for drilling bores in the ridge 12. The jig bushing 14 is arcuate, the degree of angle determined by the intended location of the prosthesis. If the prosthesis is intended to extend over the entire lower jaw, the jig bushing 14 can be U-shaped to conform to the patient's entire mandibular ridge. If the prosthesis is intended to be inserted in the front part of the lower jaw, the jig bushing 14 can be C-shaped. Alternatively, the jig bushing 14 can be J-shaped or nearly straight, as is desired. Multiple apertures 16 are formed in the jig bushing 14. The apertures 16 extend completely through the jig bushing 14 and can be positioned at any location on the jig bushing 14. The jig bushing 14 can be made of any material suitable for placement in a patient's mouth. Examples of such materials include titanium, stainless steel and plastic. The apertures 16 of the jig bushing 14 act as guides for drilling bores in the patient's maxilla (not shown) or mandibular ridge 12. The base plate 10 can be vacuum-formed of any acrylic resin appropriate for insertion in the patient's mouth.

Figure 7:
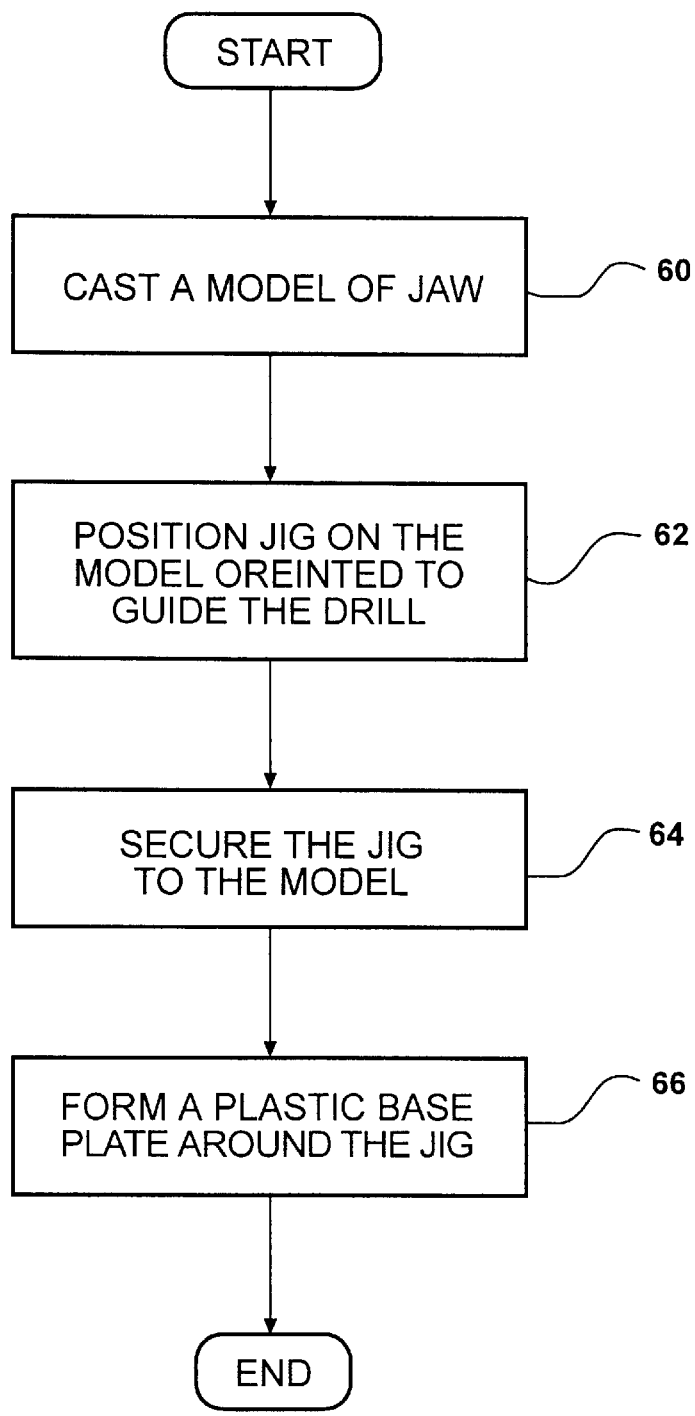
FIG. 7 is a flow chart detailing the steps for forming a base plate according to the present invention.
Figure 8:
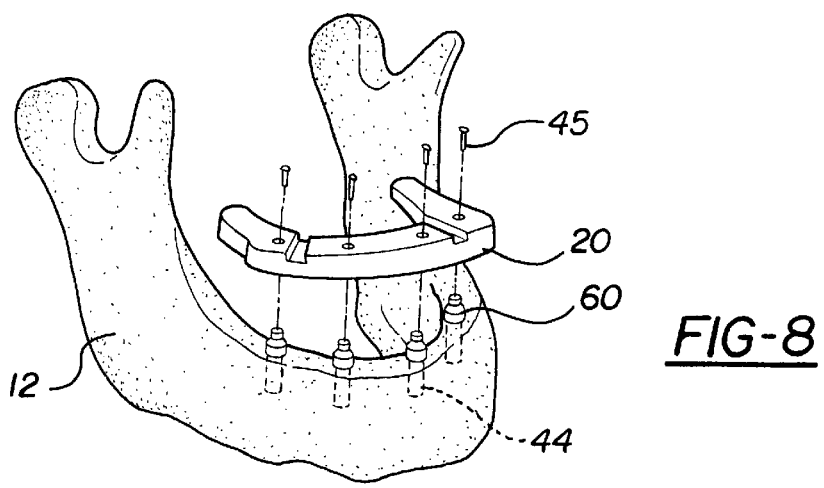
FIG. 8 is an exploded isometric view of a top plate mounted on the ride of a patent.
Figure 9:
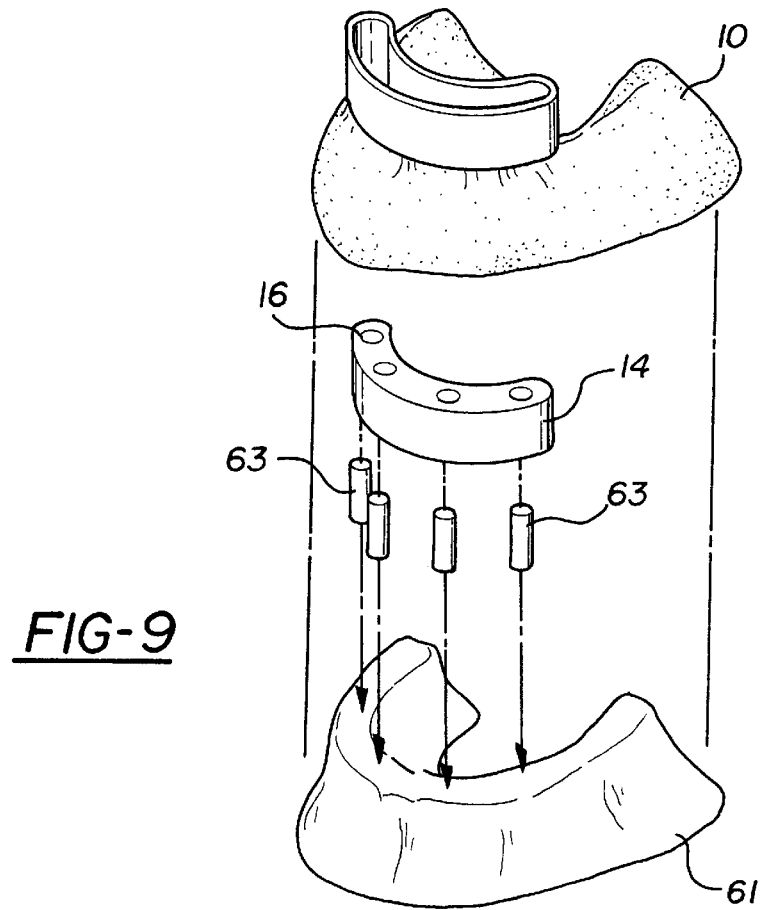
FIG. 9 is an exploded isometric view of a base plate and jig bushing mounted on the model of the jaw.

FIGS. 7 and 9 illustrate a process for forming a base plate according to the present invention. In step 60, a model 61 is cast corresponding to the form of the patient's maxilla (not shown) or mandibular ridge 12 to be subjected to the implantation procedure. In step 62, the jig bushing 14 is placed on the model. The position of the jig bushing 14 relative to the model can be adjusted before the base plate 10 is formed. The configuration and orientation of the prosthesis is determined prior to the forming of the base plate. A top plate 20 can be positioned over the model to assist in determining the appropriate configuration and orientation of the prosthesis to be mounted. The top plate 20 will support the prosthesis to be inserted into the patient's mouth, such as false teeth 22. Step 64 secures the jig bushing 14 with respect to the model. When the desired position and orientation of the jig bushing 14 relative to the model has been determined, step 66 dispenses acrylic resin over the jig bushing 14 and model to maintain the orientation of the apertures 16 relative to the model. The jig bushing 14 can be held in place relative to the model with high-temperature wax. In addition or alternatively, the jig bushing 14 can be held in place relative to the model by drilling a bore through at least one of the apertures 16 into the model and inserting a pin 63 in each bore.

Figure 4:
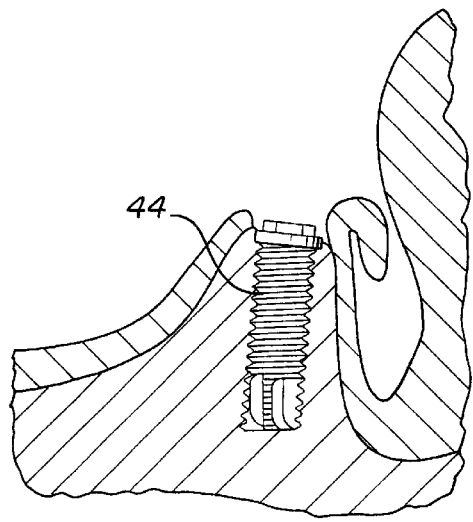
FIG. 4 is a cross-sectional view of a dental implant inserted in the bore.
Figure 5:
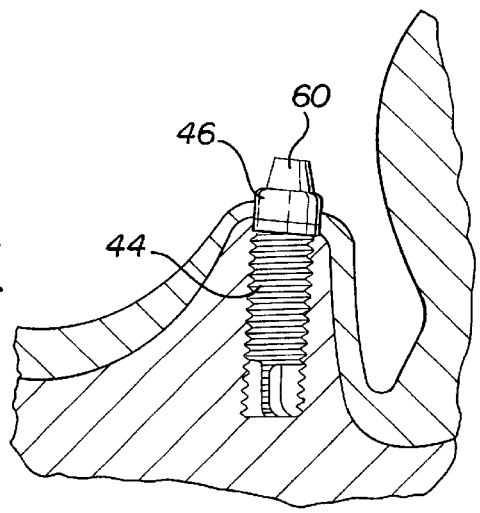
FIG. 5 is a cross-sectional view of a transmucosal adaptor mounted on the implant.
Figure 6:
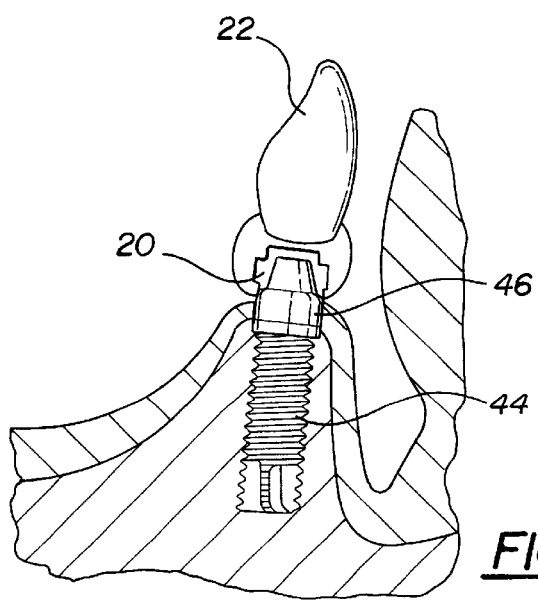
FIG. 6 is a cross-sectional view of a denture mounted on implants.

In operation, the base plate 10 is engaged with the maxilla (not shown) or mandibular ridge 12 of the patient. In a surgical procedure for inserting a root form dental implant to a mandibular ridge, an intra-oral incision can be made in the attached mucosal in the intermental foramen region so that a flap can be elevated, as shown in FIG. 4. Alternatively, the soft tissue can be punched partially or completely out. The base plate 10 is placed on the mandibular edentulous ridge 12 with the jig bushing 14 retained. This is done over distracted, soft tissue flaps or the punched region. The engagement of the base plate 10 with the ridge 12 can be enhanced by positioning a rubber block between the base plate 10 and the patient's lower or upper jaw depending on the ridge on which the procedure is being performed. The patient can bite down on the rubber block to further enhance the stability of the base plate 10 with respect to the ridge 12, as shown in FIGS. 1-3. Alternatively, the stability of the base plate 10 can be enhanced by drilling a bore through the periphery of the base plate 10 into the ridge 12 in the regions of the interior or buccal flanges and inserting a screw or nail 24 into the ridge 12. Alternatively, the base plate 10 can be held in position by a technical surgical assistant, sometimes referred to as a TSA.

When the base plate 10 and jig bushing 14 have been engaged with the ridge 12, a surgical operation can be performed on the ridge 12. In particular, a drilling operation and tapping operation can be performed. The present invention provides means 25 for drilling or tapping a bore in the ridge 12. The drilling means 25 can include a rotary motor or drive source engageable with a drill bit through a drill bit adaptor 26. The drill bit adaptor 26 can include a body 28 selectively insertable in each aperture 16 of the jig bushing 14. The aperture 16 guides the travel of the body 28. The body 28 includes means 30 for selectively retaining one of a plurality of rotary tools. A rotary tool, such as a drill bit 32, is receivable in the retaining means 30. The drill bit adaptor 26 also includes a shaft 34 engagable with an external rotary power source, such as an electric motor, a pneumatic motor or a hydraulic motor. The body 28 can also include at least one annular recess 36. Preferably, a plurality of annular recesses 36 are positioned along a longitudinal length of the elongate body 28. The annular recess 36 can receive an E-ring 38 for stopping further ingress of the body 28 into the aperture 16. The E-ring 38 can be positioned in any of the annular recesses 36 to control the depth of travel of the body 28 in the aperture 16 providing an adjustable control of the depth of the bore drilled into the ridge 12. The drilling means can also include means for supplying internal irrigation to a cutting end 40 of the drill bit 32. FIG. 3 shows a bore 37 drilled in a patient's ridge 12.

In operation, a drill bit 32 is inserted in the receiving means 30 of the body 28. The E-ring 38 is positioned on one of the annular recesses 36 of the body 28 corresponding to a desired drilling depth. An external power source is engaged with the shaft 34 to rotate the drill bit 32. The drill bit 32 is inserted in the aperture 16 of the jig bushing 14 and bores an aperture 37 in the ridge 12. The body 28 is inserted into the aperture 16 and passes through the aperture 16 until the E-ring 38 presses against the jig bushing 14. After a first bore 42 is drilled into the ridge 12, a stabilizing pin can be placed in the first bore 42. A second bore can be drilled into the ridge 12 in a similar manner as was the first bore 42. Each bore can be drilled with a series of successively larger drill bits. When all of the desired bores have been drilled to the desired size and depth, the bores are finished by tapping the bores with a tapping bit. After the bores are tapped, the base plate 10 can be removed from the patient's mouth and implants 44 can be screwed into the bores. The intra-oral incision of the bores can be debrided. Transmucosal adaptors 46 can be added to each implant 54. Retaining screws 45 can connect the implants 44, the transmucosal adaptors 46 and the top plate 20. The transmucosal adaptors 56 have a sloped end 60 protruding from the patient's ridge 12. The top plate 20 or other prosthodontic connectors can be seated on the sloped end 60. The height of a transmucosal adaptor can be varied based on the condition of the patient's mouth as can the length of the retaining screws. A fixed or removable bridge prosthesis, fabricated using generally accepted prosthodontic procedures, can be fabricated using a top plate 20 or other connectors as a supporting framework.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for mounting a dental prosthesis to an upper or lower jaw of a patient comprising the steps of:

mounting a jug with respect to the jaw and in a mouth of the patient and defining a plurality of apertures extending therethrough; and holding the jig with respect to the jaw of the patient during drilling of at least one bore to be created with a base plate having a mounting surface corresponding to a configuration of the jaw of the patient and a support surface for receiving the jig, at least one of the apertures of the jig corresponding to a configuration of the at least one bore to be drilled in the jaw of the patient when the jig and the base plate are engaged and mounted on the jaw, wherein the plurality of apertures defined by the jig are in a predetermined position and immovable with respect to one another prior to engagement of the jig and the base plate.

2. The method of claim 1 further comprising the steps of:

casting a model of the jaw of the patient;

positioning the jig on the model at a first position so that the at least one aperture is oriented to guide the path of travel of a rotary tool during the drilling step; and forming a plastic base plate over and around the jig to maintain the first position of the jig relative to the configuration of the jaw.

3. The method of claim 2 further comprising the step of:

securing the jig to the model prior to the forming step.

4. The method of claim 3 wherein the securing step further comprises the step of:

mounting the jig to the model with wax.

5. The method of claim 2 further comprising the step of:

securing the engaged jig and base plate to the jaw prior to drilling a bore in the jaw.

6. The method of claim 5 wherein the securing step further comprises the step of:

drilling a bore through the base plate and piercing the jaw of the patient; and inserting a fastener in the bore.

7. The method of claim 1 further comprising the step of:

displacing soft tissue at a position of the jaw where the at least one bore is to be drilled.

8. The method of claim 1 further comprising the steps of:

inserting a first end of an implant in the at least one bore, the implant having a second end opposite from the first end;

engaging an engaging end of an adapter to the second end of the implant, the adaptor having a sloped seating end opposite from the engaging end of the adaptor; and mounting a prosthodontic connector to the seating end of the adapter, the prosthodontic connector for retaining the prosthesis to be mounted to the jaw.

9. The method of claim 8 wherein the mounting step further comprises the step of:

joining the prosthodontic connector to the adaptor with at least one retaining screw.

10. The method of claim 1 further comprising the step of:

drilling at least one bore of predetermined depth in the jaw of the patient with drilling means, the drilling means insertable through one of the apertures of the jig.

11. The method of claim 10 wherein the drilling step further comprises the steps of:

selectively engaging a drill bit with a drill bit adaptor;

selectively inserting the drill bit in the at least one aperture of the jig; and adjustably limiting a depth of insertion of the drill bit adaptor in the at least one aperture.

12. The method of claim 10 wherein the drilling step further comprises the steps of:

drilling a first bore in the jaw of the patient with drilling means through the at least one aperture of the jig; and inserting a pin in the first bore to secure the base plate relative to the jaw of the patient during subsequent drilling.

13. A method for mounting a dental prosthesis to an upper or lower jaw of a patient comprising the steps of:

mounting a jig with respect to the jaw and in a mouth of the patient and defining a plurality of apertures extending therethrough;

holding the jig with respect to the jaw of the patient during drilling of at least one bore to be created with a base plate having a mounting surface corresponding to a configuration of the jaw of the patient and a support surface for receiving the jig, at least one of the apertures of the jig corresponding to a configuration of the at least one bore to be drilled in the jaw of the patient when the jig and the base plate are engaged and mounted on the jaw;

casting a model of the jaw of the patient;

positioning the jig on the model at a first position so that the at least one aperture is oriented to guide the path of travel of a rotary tool during the drilling step;

forming a plastic base plate around the jig to maintain the first position of the jig relative to the configuration of the jaw; and securing the jig to the model prior to the forming step by drilling a bore in the model, the bore in alignment with the at least one aperture, and inserting a pin in the at least one aperture, the pin extending through the jig and penetrating the bore.

14. A method for mounting a dental prosthesis comprising the steps of:

casting a model replicating a shape of a jaw of a patient to receive the prosthesis;

mounting a jig to the model, the jig having a plurality of apertures therethrough; and dispensing plastic over the model and jig, the plastic conforming to the model and the jig when initially dispensed, and the plastic becoming immovably associated with the jig after setting, wherein the plurality of apertures defined by the jig are in a predetermined position and immovable with respect to one another prior to the plastic becoming immovably associated.

* * * * *